United States Patent
Metcalfe et al.

(10) Patent No.: US 8,512,410 B2
(45) Date of Patent: Aug. 20, 2013

(54) STEMLESS SHOULDER IMPLANT

(75) Inventors: Nick J. T. Metcalfe, Munich (DE);
Gerlinde Michel, Munich (DE)

(73) Assignee: Arthex, Inc., Naples, FL (US)

( * ) Notice: Subject to any disclaimer, the term of this patent is extended or adjusted under 35 U.S.C. 154(b) by 0 days.

(21) Appl. No.: 13/347,311

(22) Filed: Jan. 10, 2012

(65) Prior Publication Data
US 2012/0179263 A1 Jul. 12, 2012

(30) Foreign Application Priority Data

Jan. 11, 2011 (EP) .................................. 11150615

(51) Int. Cl.
*A61F 2/40* (2006.01)
(52) U.S. Cl.
USPC ...................................... 623/19.14
(58) Field of Classification Search
USPC ................... 623/19.11–19.14, 22.31
See application file for complete search history.

(56) References Cited

U.S. PATENT DOCUMENTS

| 7,819,923 B2 | 10/2010 | Stone et al. |
| 2009/0210065 A1 | 8/2009 | Nerot et al. |

FOREIGN PATENT DOCUMENTS

| CH | 677072 A5 | 4/1991 |
| DE | 197 55 246 C1 | 3/2000 |
| DE | 20 2009 011 293 U1 | 12/2009 |
| EP | 0 299 889 A2 | 1/1989 |
| EP | 0 578 345 A1 | 1/1994 |
| FR | 2 876 899 A1 | 4/2006 |
| WO | WO 03/005933 A2 | 1/2003 |
| WO | WO 2007/041879 A1 | 4/2007 |
| WO | WO 2009/143057 A2 | 11/2009 |

*Primary Examiner* — David H Willse
*Assistant Examiner* — Javier Blanco
(74) *Attorney, Agent, or Firm* — Dickstein Shapiro LLP (57) ABSTRACT

A humerus implant for a reverse shoulder prosthesis has a cup shaped body and a thread at the outside of the body. The thread has a plurality of fins with cut-outs between the fins. At least one fin has an inclined leading surface which helps in incising into the bone by rotating the body in an inward direction. Furthermore, at least one fin has a forward oriented undercut trailing surface blocking rotation in the outward direction.

7 Claims, 8 Drawing Sheets

STEMLESS SHOULDER IMPLANT

FIELD OF THE INVENTION

The present invention relates to a shoulder arthroplasty system to surgical reconstitution of the shoulder and, in particular, to a humerus implant.

BACKGROUND OF THE INVENTION

The shoulder joint is a ball-and-socket joint which has an exceptional range of motion. Shoulder instability and other maladies of the shoulder joint, such as arthrosis or fracture, may require a replacement of the joint.

A shoulder joint prosthesis which includes the replacement of the convex head of the humerus is disclosed in U.S. Pat. No. 7,819,923. It reflects the orientation and the center of rotation of actual joints. In the case of a worn or damaged rotator cuff or too much bone loss such a prosthesis would not recover the range of motion. In such a case a reverse shoulder prosthesis may be preferable. An example of such a prosthesis is disclosed in the U.S. patent application Publication No. 2009/0210065 A1. In such a prosthesis, the humeral component includes a stem and a cup attached to the stem. The glenoid component supports a convex head which articulates with the cup of the humeral component. For inserting the stem into the humerus a significant amount of bone substance has to be removed. This complicates later revision due to the low remaining bone volume.

An implant as disclosed in the U.S. patent application Publication No. 2009/0306782 A1 (WO 2007/041879) requires only a minimum of bone material to be removed. Here fixation of the implant within the bone is far less stable compared to a stem. EP 0578 345 A1 discloses an acetabular cup having an outer thread. CH 677 072 A5 discloses a further joint prosthesis with an outer thread.

SUMMARY OF THE INVENTION

The problem to be solved by the invention is to provide a humerus implant which may be used as part of a shoulder prosthesis and which can be securely fixed within the humerus with minimal removal of bone material. A good fixation shall be achieved immediately after insertion, without cementing, so that the joint can be used immediately after insertion.

Solutions of the problem are described in the independent claim. The dependent claims relate to further improvements of the invention.

In an embodiment the humerus implant has a cup shaped body (10) having side walls between a top side (11) and a bottom side (12). At the outside of the body is a thread (13) having a plurality of fins starting with a first fin (14) and ending with a last fin (15). There are cutouts (16) between the fins. The fins are specifically designed to secure the body within the bone (30) even without cementing. Due to the radial anchoring in the bone material the fins cause a comparatively high pull out force of the implant. At least one fin, preferably a plurality of fins, most preferably all fins have an inclined leading surface (21) which helps in incising into the bone by rotating the body in an inward direction. By this measure the insertion torque is minimized. The inclination of the leading surface (21) may also be negative resulting in an undercut leading surface (21). There may be a combination of different types of fins in one thread. Furthermore at least one fin, preferably a plurality of fins, most preferably all fins have a forward oriented undercut trailing surface (25). This results in an angle of less than 90 degrees between a top surface (23) and the trailing surface (25), blocking rotation in the opposite, outward direction. Therefore the removal torque is maximized. Between the individual fins there are cutouts leaving room for abraded bone material and therefore further reducing the insertion torque and avoiding chattering. Tests have proven that this thread design results in removal torques similar to and preferably at least 60% of insertion torques immediately after insertion and without any recovery period allowing further bone growth into the structure. Due to such bone growth the removal torque increases further with time.

It is further preferable, if the top surface (23) is also slightly inclining. It is preferred to have approximately straight leading, top and trailing surfaces, although any one or multiple surfaces may be rounded or arc shaped, which may result in a sawtooth like design.

By filling the cutouts with cement or bone grafts or substitutes the stability may further be increased.

In a preferred embodiment at least one fin, preferably a plurality of fins, most preferably all fins extend in a radial direction from the cup shaped body.

In a further embodiment the depth of the fins increase from the first fin (14) to the last fin (15). So the last fin has more depth than the first fin. This further decreases insertion torque and increases stability.

A further improvement of these characteristics may be achieved by decreasing thickness of the fins from the first fin (14) to the last fin (15). Accordingly the first fin is the thickest one while the last fin is the thinnest one. This helps to compress cancellous bone into the required thread form to maximize retention between fins. The fins may also have more thickness at the base connected to the cup shaped body and less thickness at the distant side.

In another embodiment the thread is a multiple start thread, preferably a two start thread or a three start thread. This allows a more precise start of screwing the thread into the bone.

In a preferred embodiment the edge (17) between the side walls and the bottom side, enclosing the bottom side is rounded. Furthermore the sides of the fin surfaces (21, 23, 25) may be rounded to reduce stress risers in the native bone stock.

In a further embodiment the bottom side (12) has at least one protuberance. Preferably it is convex shaped thus further extending in height from the side walls. This helps to dissipate seating forces. Furthermore the implant is easier to be inserted into the bone. Screwing in an implant having a planar bottom side, is very difficult. Rotation must be stopped before or exactly when the bottom side (12) contacts the bottom side of the excavation in the bone. By further rotation the thread would become stripped, or the bone material would get at least cracks significantly reducing stability and increasing healing time. Here rotation must be stopped immediately, thus allowing no corrections of the rotational angle. This cannot happen with a convex surface or a surface having protuberances. Here the at least one protuberance would first contact the bone surface at the bottom side of the excavation and would generate a counterforce increasing with further rotation. This signals the surgeon to stop rotation.

In a further embodiment the bottom side (12) is elastic to axial pressure from the outside of the cup shaped body. Preferably the elasticity is selected such that the bottom side will be compressed before the thread is torn during screwing in the implant. Furthermore due to the elasticity corrections can be made to place the implant at the correct rotational angle. Also seating of the thread is improved and removal torque is increased due to the pre-load.

The humerus implant may directly interface with the glenoid component of a reverse (inverse) shoulder prosthesis. It may also be designed to hold a joint adapter to interface with the glenoid component of a reverse shoulder prosthesis. In this case the joint adapter is inserted into the cup shaped body. It may furthermore be designed to hold the humerus component of an anatomical prosthesis.

In another embodiment the humerus implant is designed to provide an interface for the humeral component of an anatomical prosthesis.

In the most preferred embodiment it is designed to provide a combination interface for a joint adapter to interface with the glenoid component of a reverse prosthesis and the humeral component of an anatomical prosthesis. Here specifically the cup shape allows a more simple and robust interface for the humeral component of an anatomical prosthesis, which for example may be held by a Morse taper. This embodiment allows simple replacement of an anatomical prosthesis by a reverse prosthesis during revision. Here exchanging of a prosthesis stem is no more necessary. Even the implant can remain in place, as only the heads must be exchanged.

The humerus implant may be manufactured from Titanium alloy, or other bio-compatible metallic or non metallic materials. The external surfaces of the device may be enhanced to allow by additive or subtractive processes, the application of texture or osteoinductive/osteoconductive material.

The humerus implant or a joint adapter may be manufactured by using Ultra High Molecular Weight Polyethylene, or other biocompatible material suitable for use as a bearing surface in concert with a mating component of complimentary geometry.

The present invention relates to a modular shoulder arthroplasty system to address preferably osteoarthritis, trauma and cuff tear arthropathy. The invention is not limited to such applications. It may also be used to replace any other joint.

BRIEF DESCRIPTION OF THE DRAWINGS

In the following the invention will be described by way of example, without limitation of the general inventive concept, on examples of embodiment with reference to the drawings.

DETAILED DESCRIPTION OF THE PREFERRED EMBODIMENTS

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

Figure 1:
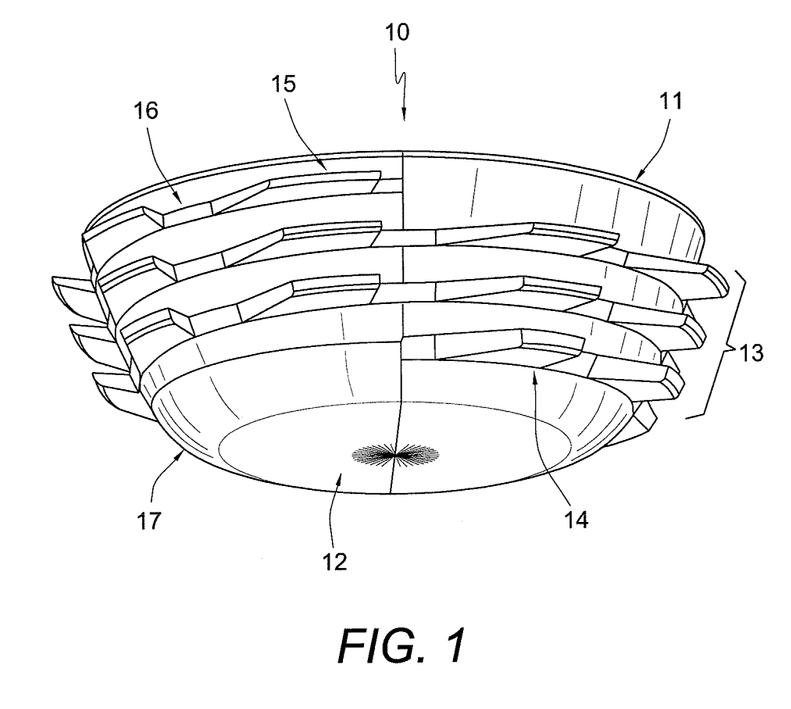
FIG. 1 shows an embodiment of a humerus implant.

FIG. 1 shows an embodiment of a humerus implant. The implant has a cup shaped body (10) having side walls between a top side (11) and a bottom side (12). At the outside of the body is a thread (13) having a plurality of fins starting with a first fin (14) and ending with a last fin (15). There are cutouts (16) between the fins. The body may be screwed clockwise as viewed from the top side into the bone. A counter clock wise oriented thread may also be provided. The edge (17) between the side walls and the bottom side, enclosing the bottom side is rounded.

Figure 2:
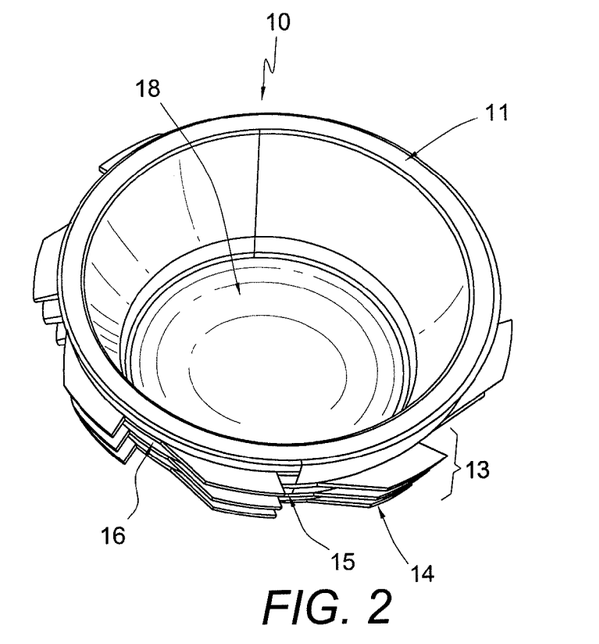
FIG. 2 shows a top view into the cup shaped body of the implant.

FIG. 2 shows a top view into the cup shaped body (10) of the implant. Here the inner bottom side (18) is visible.

Figure 3:
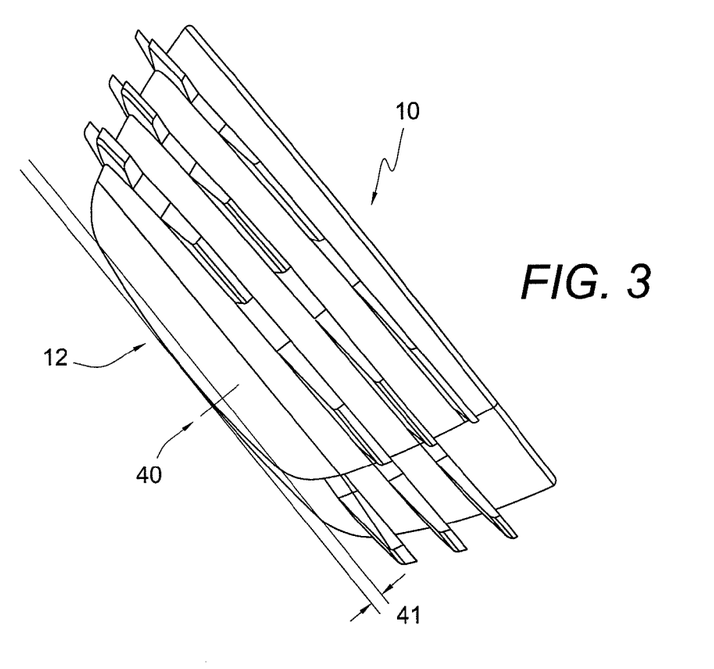
FIG. 3 shows details of a convex bottom side.

FIG. 3 shows details of a convex bottom side (12). The bottom side has at least one point (40) with a maximum extension over the side walls. The height (41) of the extension over the side walls may be adapted together with the elasticity of the material to the desired range of rotation between the first contact and maximum compression. It is preferred to have only one maximum extension point, but there may also be a plurality of such points resulting in a bottom side surface with multiple protuberances.

Figure 4:
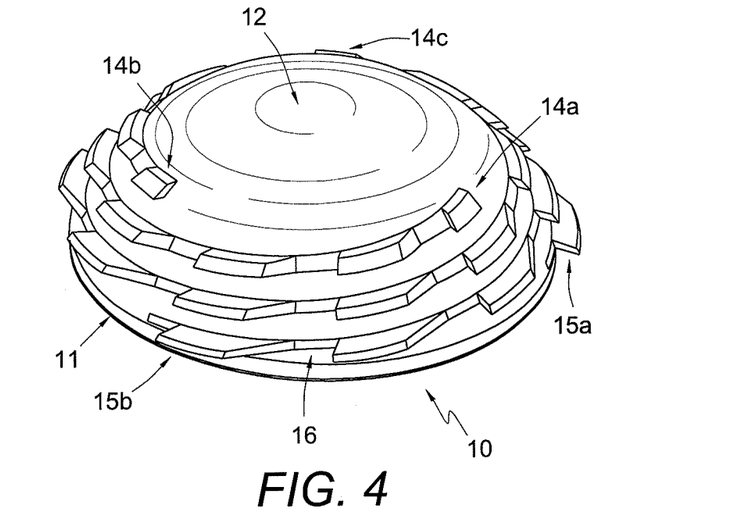
FIG. 4 shows an embodiment with a three start thread.

FIG. 4 shows an embodiment with a three start thread. The thread has three starts (14a, 14b, 14c) and three ends (15a, 15b)—the third end is not visible.

Figure 5:
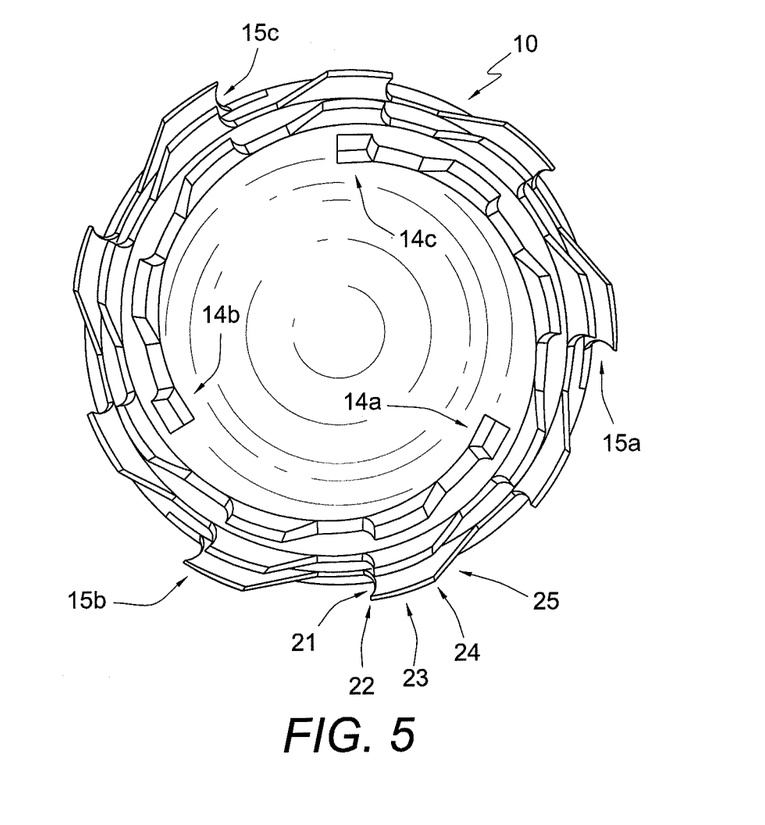
FIG. 5 shows an embodiment with a modified three start thread.

FIG. 5 shows an embodiment with a modified three start thread. The individual fins have an exaggerated non linear trailing barb edge (21). The thread has three starts (14a, 14b, 14c) and three ends (15a, 15b, 15c).

Figure 6:
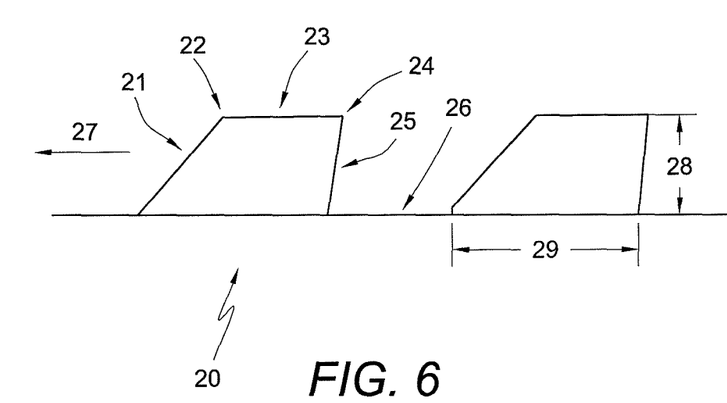
FIG. 6 shows individual fins of a thread.

FIG. 6 shows individual fins of the thread (13). A first fin (20) which may be any one of the fins between the first fin (14) and the last fin (15) is moved in the indicated direction (27) when screwed into the bone. For improved cutting and decreased insertion torque the fin has a first inclined leading surface (21) for cutting a thread into the bone and a slightly rounded leading edge (22) to the top surface (23) of the fin. At the end of the top surface is a preferably sharp trailing edge (24) to a forward oriented trailing surface (25) thus defining an angle of less than 90 degrees between the top surface (23) and the trailing surface (25). This increases removal torque significantly. Between the individual fins there are cut-outs (26, 16). Each individual fin is further characterized by its depth (28), its length (29), and its thickness extending into the drawing plane which is not shown here.

Figure 7:
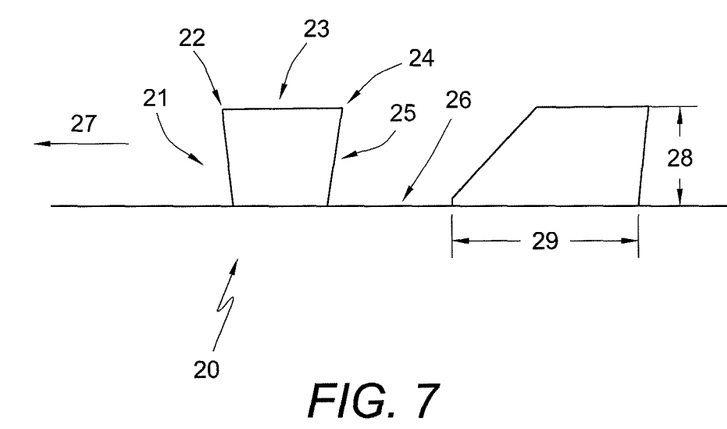
FIG. 7 shows individual fins of a modified thread.

FIG. 7 shows individual fins of a modified thread. For further improved cutting the leftmost fin has a first declined undercut leading surface (21), having an angle less than 90 degrees between the leading surface (21) and the top surface (23). This example shows the combination of two different types of fins.

Figure 8:
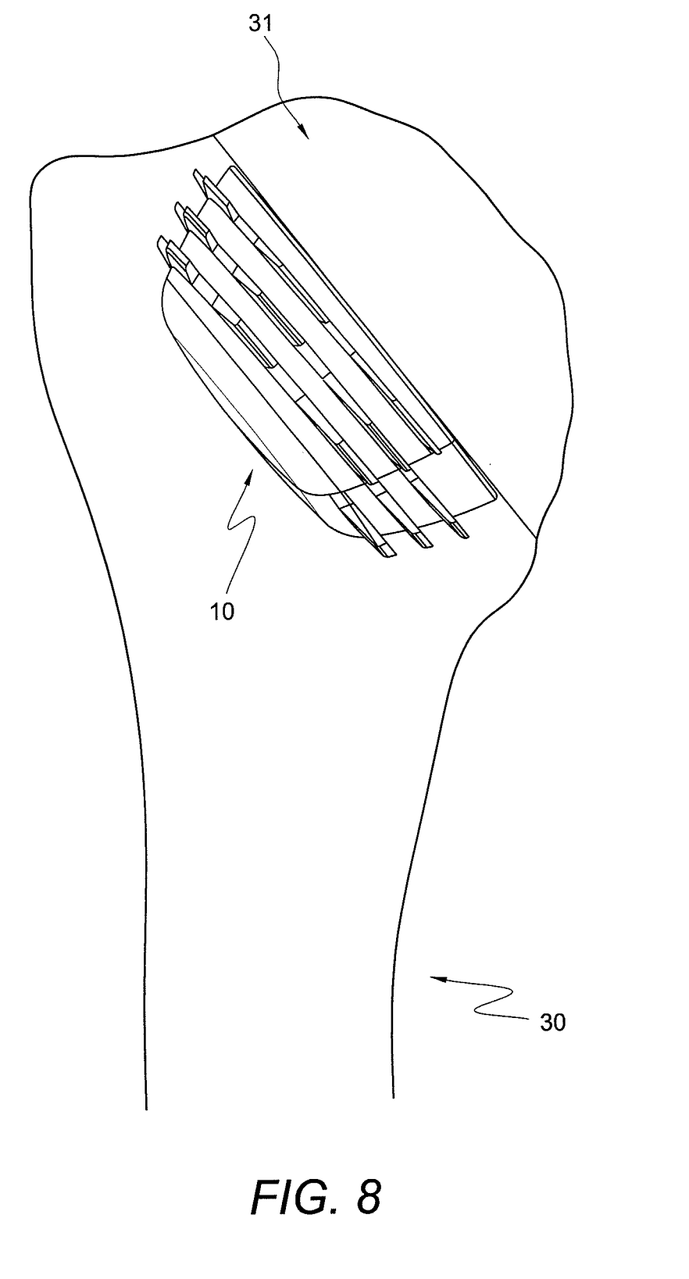
FIG. 8 shows a humerus with an inserted implant.

FIG. 8 shows a humerus (30) with an inserted implant body (10) in the cancellous bone. Before insertion of the implant the top section (31) of the humerus head has to be resected and an excavation for the body must be made. The optimum position of the implant can be selected by the position and angle under which the top section (31) of the humerus is cut away.

Figure 9:
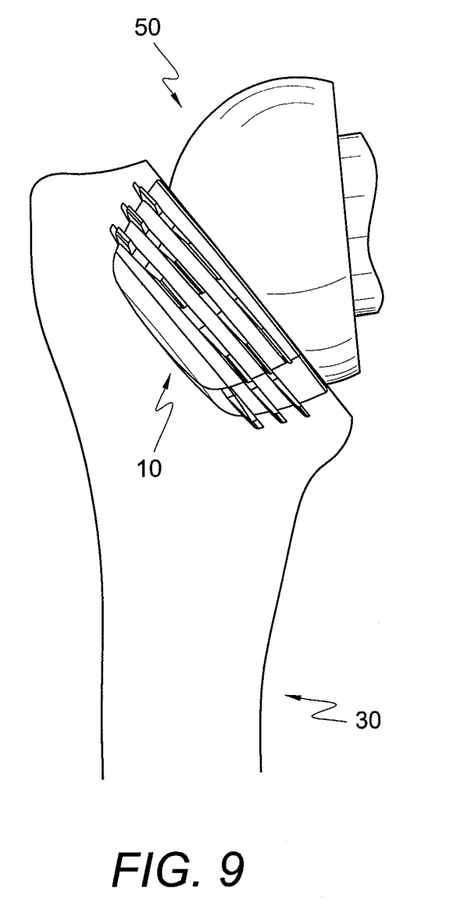
FIG. 9 shows a glenoid component at the implant body.

FIG. 9 shows a glenoid component (50) of a reverse shoulder prosthesis (also referred as inverse shoulder prosthesis) mounted into the implant body (10).

Figure 10:
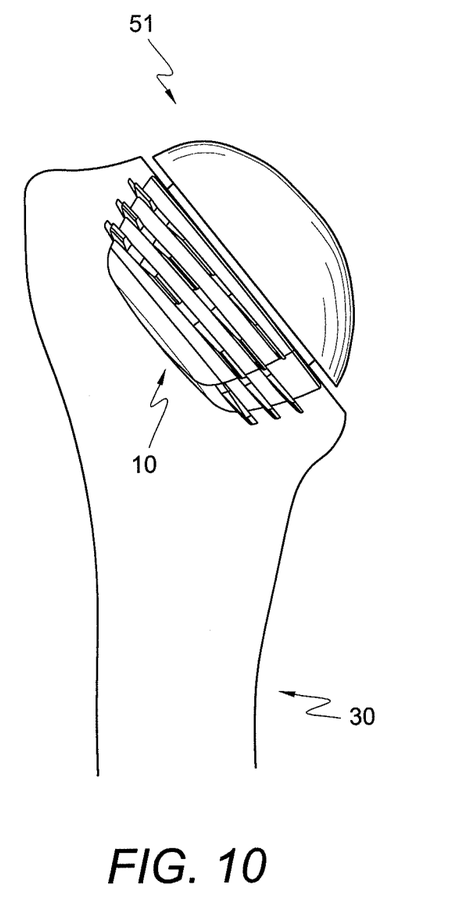
FIG. 10 shows a humerus component at the implant body.

FIG. 10 shows a humerus component (51) of an anatomical prosthesis mounted into the implant body (10).

Figure 11:
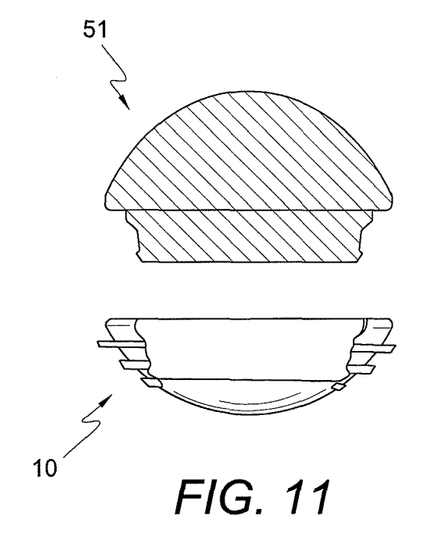
FIG. 11 shows a humerus component at the implant body in a cross sectional view.

FIG. 11 shows a humerus component (51) of an anatomical prosthesis mounted into the implant body (10) in cross sectional view. The humerus component is snapped into the implant body.

Figure 12:
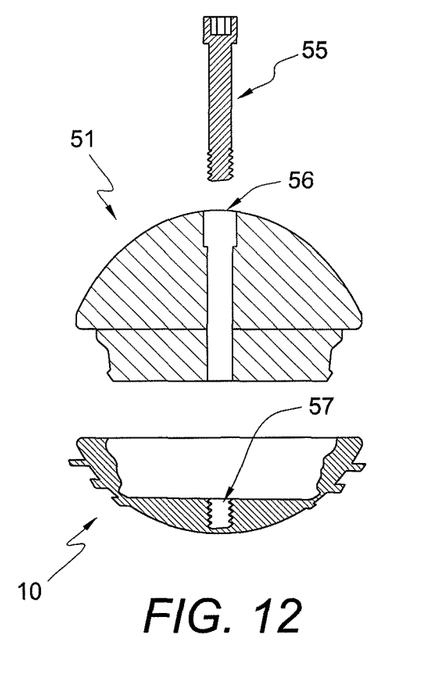
FIG. 12 shows another humerus component at the implant body in a cross sectional view.

FIG. 12 shows a humerus component (51) of an anatomical prosthesis mounted into the implant body (10) in cross sectional view. The humerus component is secured by a screw (55) inserted through a hole (56) in the humerus component and a thread (57) in the implant body.

Figure 13:
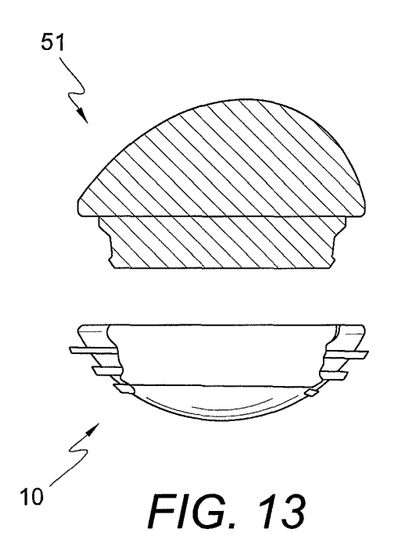
FIG. 13 shows a humerus component adapted to anatomical requirements.
Figure 14:
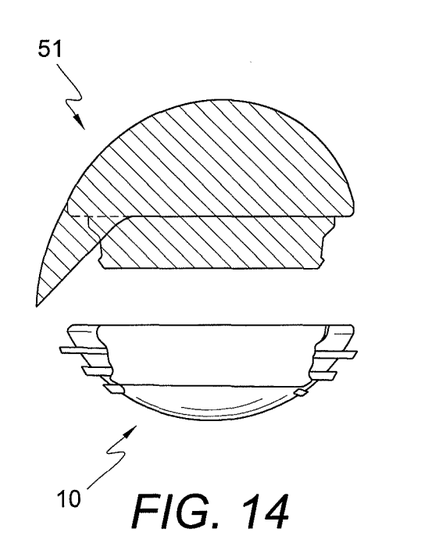
FIG. 14 shows another humerus component adapted to anatomical requirements.

FIGS. 13 and 14 show different embodiments of a humerus component (51) of an anatomical prosthesis mounted into the implant body (10) in cross sectional view. The humerus component is adapted to anatomical requirements.

Figure 15:
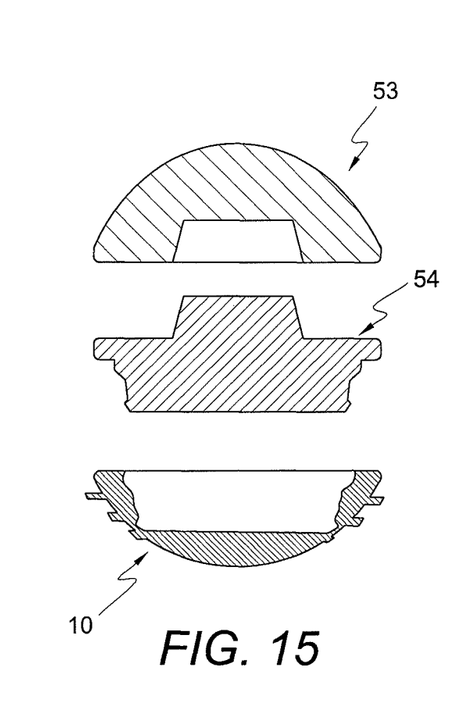
FIG. 15 shows a humerus component mounted by an adapter.
Figure 16:
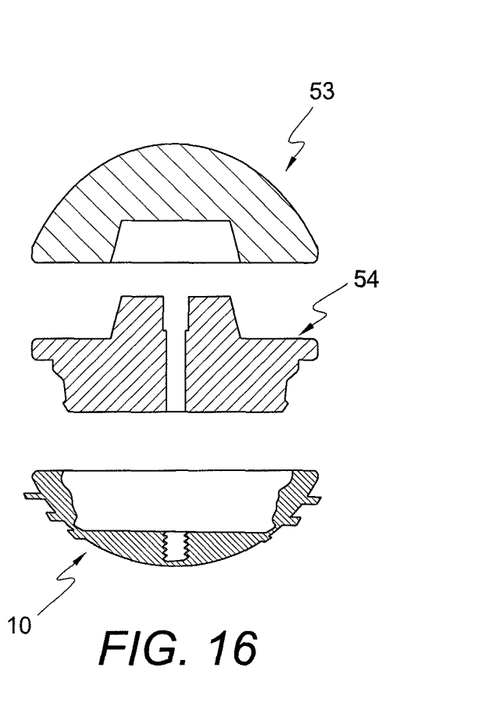
FIG. 16 shows another humerus component mounted by an adapter.

FIGS. 15 and 16 show different embodiments of a humerus component (53) of an anatomical prosthesis mounted into the implant body (10) by means of an adapter (54) shaped like a trunion. The adapter of FIG. 16 is a split adapter comprising of at least two, preferably 3 or 4 parts.

Figure 17:
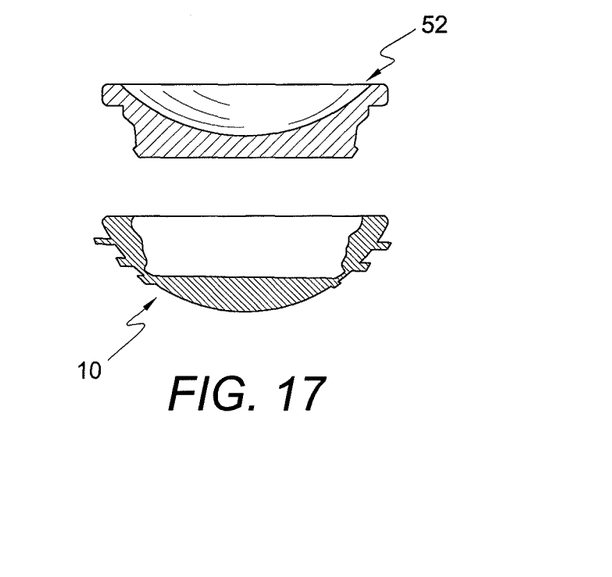
FIG. 17 shows a humerus component of a reverse prosthesis in cross sectional view.

FIG. 17 shows a humerus component (52) of a reverse prosthesis mounted into the implant body (10) in cross sectional view.

It will be appreciated to those skilled in the art having the benefit of this disclosure that this invention is believed to provide a stemless reverse shoulder implant. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A stemless humerus implant adapted to be securely fixed within the humerus of a patient with minimal removal of bone material, said stemless humerus implant having a cup shaped body (10) having sidewalls between an open top side (11) and a convex bottom side (12),
   the cup shaped body further comprising a multiple start thread (13) extending radially from the sidewalls of the body, said multiple start thread comprised by:
   a plurality of fins (14, 15) starting with a first fin (14) disposed in proximity to the convex bottom side and ending with a last fin (15) disposed in proximity to the top side, with cutouts (16) between the fins;
   each of the plurality of fins (14, 15) having an inclined leading surface (21) which helps in incising into the bone by rotating the body in an inward direction;
   each of the plurality of fins further having a forward oriented undercut trailing surface (25) resulting in an angle of less than 90 degrees between a top surface (23) and the trailing surface (25) blocking rotation in the outward direction,
   wherein depth of the fins increase from the first fin (14) to the last fin (15),
   wherein thickness of the fins decrease from the first fin (14) to the last fin (15), and
   wherein at least one of surfaces (21, 23, 25) of the fins are rounded to reduce stress risers in the native bone stock.

2. The stemless humerus implant according to claim 1, wherein the thread (13) is selected from the group consisting of a two start thread and a three start thread.

3. The stemless humerus implant according to claim 1, wherein the bottom side (12) is convex shaped to dissipate seating forces.

4. The stemless humerus implant according to claim 1, wherein the humerus implant directly interfaces with the glenoid component of a shoulder prosthesis.

5. The stemless humerus implant according to claim 1, wherein the humerus implant holds a joint adapter to interface with the glenoid component of a shoulder prosthesis.

6. The stemless humerus implant according to claim 1, wherein the humerus implant holds the humeral component of an anatomical prosthesis.

7. The stemless humerus implant according to claim 1, wherein the humerus implant holds an interface for a joint adapter to interface with the glenoid component of a shoulder prosthesis and to hold the humerus component of an anatomical prosthesis.

* * * * *

UNITED STATES PATENT AND TRADEMARK OFFICE
CERTIFICATE OF CORRECTION

PATENT NO. : 8,512,410 B2
APPLICATION NO. : 13/347311
DATED : August 20, 2013
INVENTOR(S) : Nick J. Metcalfe et al.

Page 1 of 1

It is certified that error appears in the above-identified patent and that said Letters Patent is hereby corrected as shown below:

On the title page, Item (73), Assignee, change "Arthex, Inc" to -- Arthrex, Inc. --

Signed and Sealed this
Twenty-fourth Day of March, 2015

Michelle K. Lee
*Director of the United States Patent and Trademark Office*